US006969356B2

(12) United States Patent
Nishibayashi

(10) Patent No.: US 6,969,356 B2
(45) Date of Patent: Nov. 29, 2005

(54) INFLATABLE CUFF FOR BLOOD PRESSURE MEASUREMENT

(75) Inventor: Hideo Nishibayashi, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 10/799,744

(22) Filed: Mar. 15, 2004

(65) Prior Publication Data

US 2004/0243008 A1 Dec. 2, 2004

(30) Foreign Application Priority Data

Mar. 20, 2003 (JP) .............................. 2003-077974

(51) Int. Cl.$^7$ ............................................... A61B 5/02
(52) U.S. Cl. ...................................... 600/499; 600/485
(58) Field of Search ................................ 600/485–499

(56) References Cited

U.S. PATENT DOCUMENTS

| | | | | |
|---|---|---|---|---|
| 1,043,521 A | * | 11/1912 | Hoobler | 600/492 |
| 3,527,204 A | * | 9/1970 | Steinbeck et al. | 600/496 |
| 3,752,148 A | * | 8/1973 | Schmalzbach | 600/499 |
| 4,572,205 A | * | 2/1986 | Sjonell | 600/499 |
| 6,336,901 B1 | * | 1/2002 | Itonaga et al. | 600/499 |
| 6,346,083 B1 | | 2/2002 | Nishibayashi et al. | |
| 6,497,668 B2 | | 12/2002 | Nishibayashi | |
| 6,527,727 B2 | * | 3/2003 | Itonaga et al. | 600/499 |
| 6,694,821 B2 | * | 2/2004 | Yamakoshi et al. | 600/490 |

FOREIGN PATENT DOCUMENTS

| | | |
|---|---|---|
| JP | U62-116703 | 7/1987 |
| JP | A-4-338450 | 11/1992 |
| JP | A 5-269089 | 10/1993 |

* cited by examiner

Primary Examiner—Max F. Hindenburg
Assistant Examiner—Patricia C. Mallari
(74) Attorney, Agent, or Firm—Oliff & Berridge PLC

(57) ABSTRACT

An inflatable cuff for blood pressure measurement includes a first inflatable bag which is inflatable to press an arterial vessel of a body portion of a living subject and stop flow of blood in the arterial vessel which the inflatable cuff is adapted to be wound around the body portion; a second inflatable bag for sensing a pulse wave propagating along the arterial vessel, which is supported by the inflatable cuff such that the second inflatable bag is located inside a downstream-side portion of the first inflatable bag in the direction of the blood flows in the arterial vessel, and which has a dimension as measured in the direction that is smaller than a dimension of the first inflatable bag as measured in said direction; and a fluid-filled bag which is located between the second inflatable bag and the body portion and which is filled with incompressible fluid.

15 Claims, 2 Drawing Sheets

INFLATABLE CUFF FOR BLOOD PRESSURE MEASUREMENT

BACKGROUND OF THE INVENTION

1. Field of the Invention

The present invention relates to an inflatable cuff for blood pressure measurement, which is adapted to be worn on a body portion of a living subject, and particularly to a cuff having a first inflatable bag for pressing the body portion and a second inflatable bag for sensing a pulse wave.

2. Description of Related Art

A cuff, including an inflatable bag, is adapted to be wound around a body portion of a living subject. The bag inflates when a gas or a liquid is supplied into, and consequently the wound cuff presses the body portion.

A cuff may function not only as a device for pressing a body portion, but also as a device for sensing a pulse wave propagating from an arterial vessel. In general, an oscillometric blood pressure measuring device slowly deflates the cuff wound around a body portion to weaken a force by the cuff against the body portion, and determines a blood pressure based on pulse waves continuously received by the cuff during the slow deflation. The device adopts a static pressure of the inflatable bag as a systolic pressure, at a rising point of an envelope of amplitudes of the pulse waves, that is, a point where the amplitude of the pulse waves suddenly raises.

The device may determine an indefinite systolic pressure when the cuff has only one inflatable bag because a fluctuation in pressure in the inflatable bag provides with indefinite rising point of the envelope of the amplitudes of the pulse waves.

To solve the above problem, JP 05-269089 A, U.S. Pat. No. 6,346,083 and U.S. Pat. No. 6,497,668 disclose a cuff having an inflatable bag for pressing a body portion so as to stop a flow of blood in an arterial vessel and an inflatable bag for sensing a pulse wave from the arterial vessel. The cuff disclosed in these references includes an outer bag for pressing the body portion and an inner bag for sensing the pulse waves. A device using this cuff provides a relatively definite systolic pressure with a relatively definite rising point of the envelope of the amplitudes of the pulse waves sensed by the inner bag, because the inner bag is substantially located in the center of and on a body portion side of the outer bag and no pulsation directly propagates to the inner bag when the arterial vessel pulsates again around an upstream end of the outer bag.

An uneven surface of the body portion, such as an ankle, is difficult to fittingly wind with the cuff. The cuff having the outer bag for pressing the body portion and the inner bag for sensing the pulse waves disclosed in the above references cannot provide with a definite systolic pressure because of an indefinite shape of the envelope of the amplitudes of the pulse waves sensed by the inner bag if the inner bag is not fully wound on the uneven surface of the body portion.

SUMMARY OF THE INVENTION

It is therefore an object of the present invention to provide an inflatable cuff for blood pressure measurement including an inflatable bag for pressing a body portion of a living subject and another inflatable bag for sensing a pulse wave, which is used for determining a definite blood pressure even if the body portion has an uneven surface.

To attain this object, the present invention provides the inflatable cuff for blood pressure measurement including: (1) a first inflatable bag which is inflatable to press an arterial vessel of a body portion of a living subject and stop flow of blood in the arterial vessel which the inflatable cuff is adapted to be wound around the body portion; (2) a second inflatable bag for sensing a pulse wave propagating along the arterial vessel, the second inflatable bag is supported by the inflatable cuff such that the second inflatable bag is located inside a downstream-side portion of the first inflatable bag as seen in the direction in which the blood flows in the arterial vessel, and which has a dimension as measured in said direction that is smaller than a dimension of the first inflate bag as measured in said direction; and (3) a fluid-filled bag which is located between the second inflatable bag and the body portion and which is filled with an incompressible fluid.

According to this feature of the present invention, the fluid-filled bag located on an inner side of the second inflatable bag receives a pressure on its inner surface when a pressure of each of the first and second inflatable bags raises with the inflatable cuff wound around the body portion of the living subject. An inner surface, that is, a surface on the body portion side, of the fluid-filled bag filled with an incompressible fluid changes its form to the same as an uneven surface of the body portion and an outer surface, that is, a surface on the second inflatable bag side, of the fluid-filled bag changes its form to the same as a form of an inner surface of the second inflatable bag by the pressure. Consequently, the shape of the envelope of the amplitudes of the pulse waves sensed through the second inflatable bag is definite and an accurate blood pressure is measured thereby because the combination of the second inflatable bag and the fluid-filled bag fits on the uneven surface of the body portion.

According to a second feature of the present invention which includes the first feature, the fluid-filled bag has a size and is located such that the fluid-filled bag is present in a whole space between the second inflatable bag and the body portion of the living subject in a state that the inflatable cuff is wound around the body portion. Consequently, the shape of the envelope of the amplitudes of the pulse waves sensed through the second inflatable bag is more definite and an accurate blood pressure is measured thereby because the combination of the second inflatable bag and the fluid-filled bag fits on the uneven surface of the body portion.

According to a third feature of the present invention which includes the first feature, the fluid-filled bag has a size and is located such that the second inflatable bag and the fluid-filled bag are overlapped in a state that the inflatable cuff is wound around the body portion. Consequently, the shape of the envelope of the amplitude of the pulse waves sensed through the second inflatable bag is most definite and an accurate blood pressure is measured thereby because the combination of the second inflatable bag and the fluid-filled bag fits on the uneven surface of the body portion and the pulse wave does not propagates from the fluid-filled bag to the first inflatable bag. If the fluid-filled bag is too large and a pulsation propagated through the fluid-filled bag is directly propagated to the first inflatable bag without propagating through the second inflatable bag, a pulse wave propagated from the living subject propagates from the fluid-filled bag not only to the second inflatable bag but also to the first inflatable bag and the pulse wave which the first inflatable bag receives further propagates to the second inflatable bag. Accordingly, the shape of the envelope of the amplitudes of the pulse waves sensed through the second inflatable bag is little definite because the pulse wave becomes distorted during the propagation through the first inflatable bag to the second inflatable bag.

BRIEF DESCRIPTION OF THE DRAWINGS

The above and optional objects, features, and advantages of the present invention will be better understood by reading the following detailed description of the exemplary embodiments of the invention when considered in conjunction with the accompanying drawings, wherein.

DETAILED DESCRIPTION OF EXEMPLARY EMBODIMENTS

Hereinafter, there will be described an inflatable cuff for blood pressure measurement embodying the present invention, by reference to the drawings.

Figure 1:
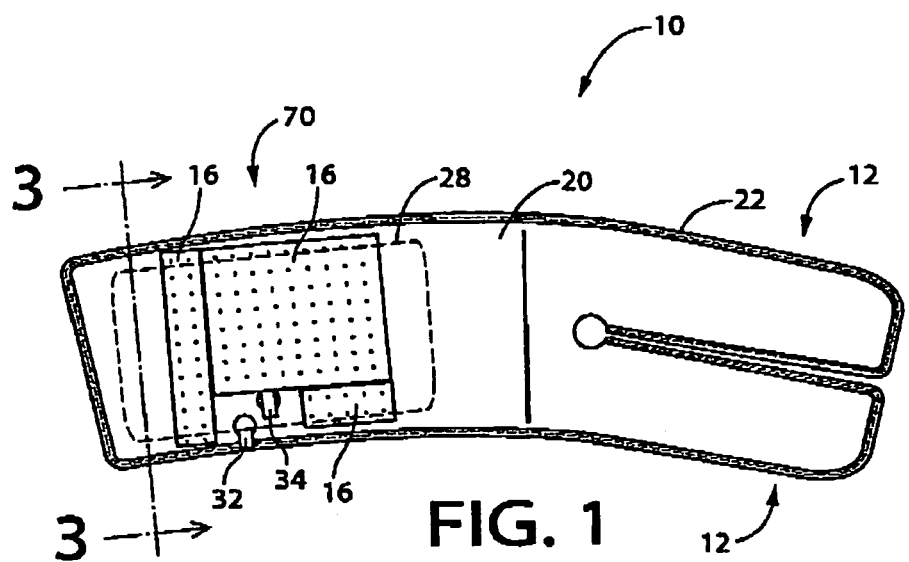
FIG. 1 illustrates an inflatable cuff for blood pressure measurement at an ankle in a plan view according to the present invention.

In FIG. 1, an inflatable cuff 10 which has a belt-like ape is about 14 cm in width and is slightly bent toward a transversal direction to be formed an arch. The cuff 10 has two narrowed portions 12, 12 at one end in a longitudinal direction. Each of the narrowed portions 12 is a half in width of the cuff 10 and has a fastener pad 14 on an inner surface, that is, a surface on a body portion side, and a main portion 70 of the cuff 10 also has fastener pads 16 on an outer surface, that is, a surface on the opposite side to the body portion side. The fastener pads 14 and 16 are fastened to each other, and the narrowed portions 12, 12 are unfastenably fixed to the main portion 70 at the fastener pads 14 and 16 with the cuff 10 wound around an ankle (not shown) and are on the most outside of the wound cuff 10. Consequently, the cuff 10 is fixed to the ankle.

A containing bag 24 consists of an inner cloth member 72 and an outer cloth member 20, both of which substantially are the same in shape as the cuff 10. The inner cloth member 72 and the outer cloth member 20 are mutually fixed by sewing with a circumferential cloth member 22. A portion of the inner cloth member 72 without the narrowed portions 12, 12 forms an inner cloth portion 18 which covers substantially from the center of the cuff 10 to the end opposite to the narrowed portion side in a longitudinal direction. The containing bag 24 includes a first inflatable bag 28 and a second inflatable bag 26, which is located in a transversal end portion, that is, on a downstream side of a blood flow in an arterial vessel and under the bag 28.

Figure 2:
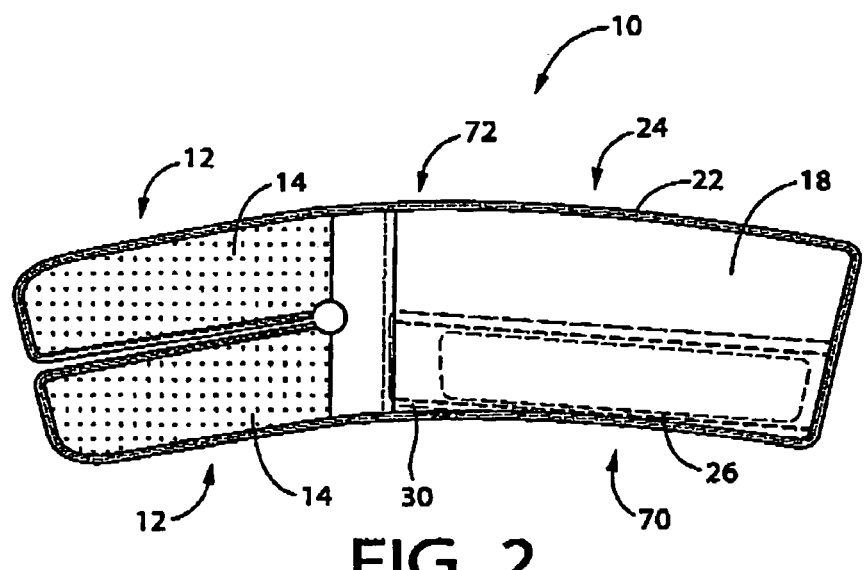
FIG. 2 illustrates the inflatable cuff for blood pressure measurement at the ankle in a bottom view.

As shown in FIG. 1, the first inflatable bag 28 for stopping the blood flow in the arterial vessel on the inner side of the cuff 10 has a rectangular shape, is slightly shorter in width than the containing bag 24, namely, than the cuff 10 and is also slightly shorter in length than the bag 24 in the longitudinal direction. As shown in FIG. 2, the second inflatable bag 26 also has a substantially rectangular shape, is about between a third and a quarter in width of the bag 24 and is slightly shorter than the bag 24 in the longitudinal direction. The bags 28 and 26 are formed of soft resin As shown in FIG. 1, the inflatable cuff 10 has a first conduit 34 integratedly connected to the first inflatable bag 28 and a second conduit 32 integratedly connected to the second inflatable bag 26. To ports of the conduits 34 and 32 protruding outside from the containing bag 24, pipes (not shown) are connected so as to supply air to the bags 28 and 26, respectively. The conduits 34 and 32 are connected each other through the pipes with a restriction.

Figure 3:
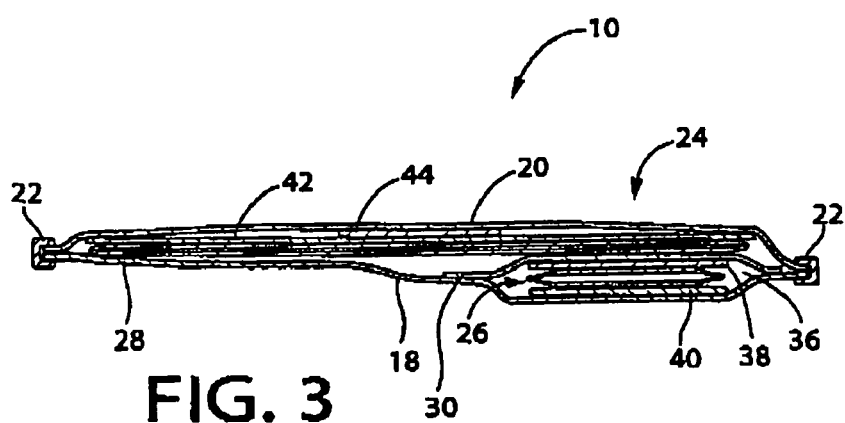
FIG. 3 illustrates the inflatable cuff for blood pressure measurement in a sectional view taken along line 3—3 in FIG. 1

As shown in FIGS. 2 and 3, the containing bag 24 includes a rectangular inner sheet 30 which has substantially the same length as the inner cloth portion 18 in the longitudinal direction and has a half length of the inner cloth portion 18 in the transversal direction. The sheet 30 is disposed such that along side of the sheet 30 on the downstream side of the blood flow in the arterial vessel when the cuff 10 is wound around the ankle is substantially located on a long side on the downstream side of the containing bag 24. Fixation of both of transversal edge portions of the sheet 30 to the inner cloth portion 18 provides with a cavity 36 which includes the second inflatable bag 26. The sheet 30 is formed of soft resin.

The cavity 36 has a shield plate 38 formed of high density polyethylene on an outer side of the bag 26 and a fluid-filled bag 40 on an inner side of the bag 26. Transversal leg of the shield plate 38 and the fluid-filled bag 40 are substantially the same as that of the second inflatable bag 26. The bag 40 is filled with an incompressible fluid, such as a gel and a liquid, while filled with water in this embodiment.

Figure 4:
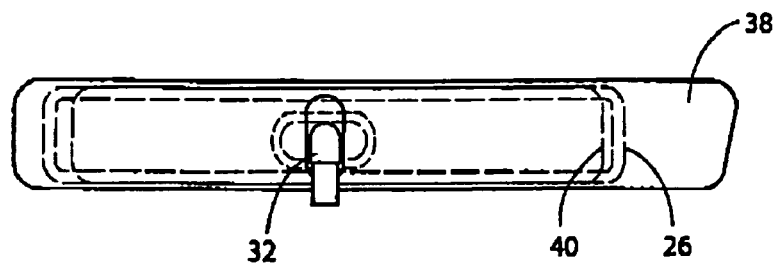
FIG. 4 illustrates a set of a first inflatable bag, a second inflatable bag and a shield plate in a plan view.

As shown in FIG. 4, the shield plate 38 has a rectangular shape whose long sides extend in the longitudinal direction. The fluid-filled bag 40 also has a rectangular shape whose long sides extend in the longitudinal direction, and is shorter than the second inflatable bag 26 in the longitudinal direction. Furthermore, the bag 40 is located parallel to the second inflatable bag 26, a width of the bag 40 is substantially equal to that of the bag 26 and a centerline of the bag 40 is on a centerline of the bag 26 in the longitudinal direction.

Figure 5:
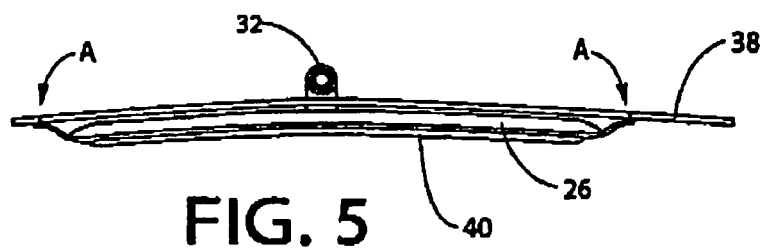
FIG. 5 illustrates the set of the first inflatable bag, the second inflatable bag and the shield plate in a front view.

As shown in FIG. 5, the shield plate 38, the second inflatable bag 26 and the fluid-filled bag 40 are integratedly fixed at respectively longitudinal ends, that is, at points A and A in the figure, one another by sewing.

The length of the fluid-filled bag 40 in the longitudinal direction is slightly shorter than that of the second inflatable bag 26 such that the bags 26 and 40 are overlapped each other when the cuff 10 is wound around the ankle. Each of the bags 26 and 40 substantially forms a part of a cylinder in a state that the cuff 10 is wound around the ankle. A radius, a distance between the center and the circumference of the cylinder, of the bag 40 is slightly shorter than that of the bag 26. Therefore, the longitudinal length of the fluid-filled bag 40 in a horizontally extended form is determined to be slightly shorter than that of the bag 26 with taking a difference of the radii.

In FIG. 3, the containing bag 24 includes the first inflatable bag 28 on the outer side of the inner sheet 30, and a first support plate 42 and a second support plate 44 on the outer side of the bag 28. The plates 42 and 44 are formed of substantially hard material, such as hard resin, to support the cuff 10 to be a cylinder shape when wound around the ankle.

Figure 6:
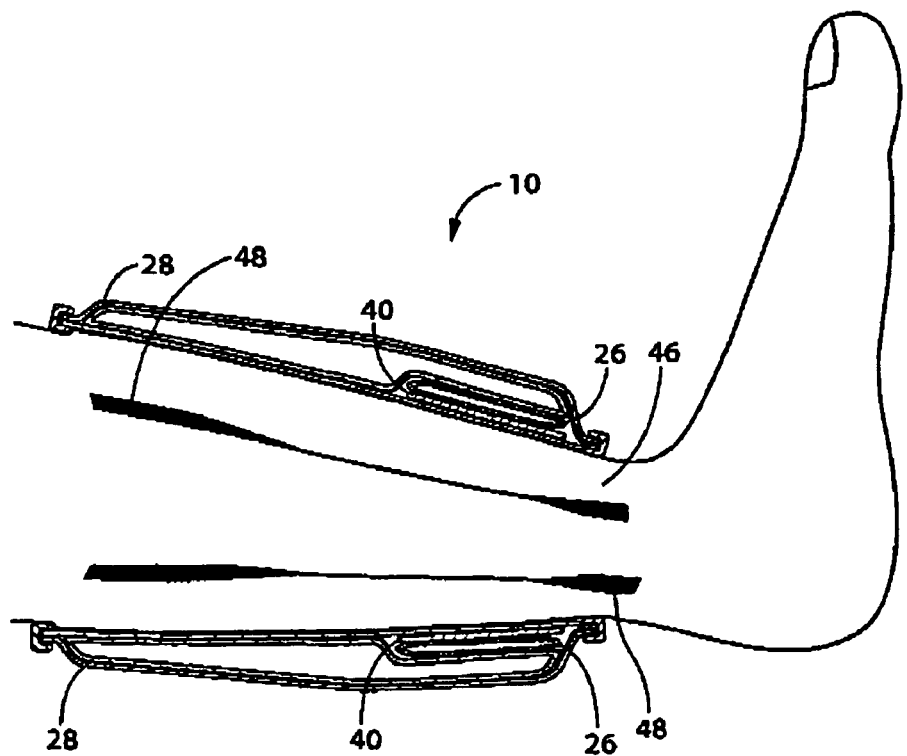
FIG. 6 illustrates the inflatable cuff wound around the ankle and arterial vessels pressed by the first and second inflatable bags.

In FIG. 6, arterial vessels 48 and 48 of an ankle 46 are pressed to stop blood flows with an inner pressure of a predetermined value, such as 250 mmHg, of each of the bags 26 and 28 for stopping the blood flow, wherein the predetermined value is over a systolic blood pressure value of the arterial vessel 48. Although the cuff 10 includes the shield plate 38, the first support plate 42 and the second support plate 44, they are not shown in FIG. 6.

The fluid-filled bag 40 and the second inflatable bag 26 are substantially overlapped in a state shown in FIG. 6 because the widths of the bags 40 and 26 are substantially equal to each other and the longitudinal length of the bag 40 are appropriately shorter than that of the bag 26 such that overlapping of the bags 40 and 26 are provided in the state that the cuff 10 is wound around the ankle 46 as described above.

In FIG. 6, the fluid-filled bag 40 filled with water changes its inner side form to the same as a form of an uneven surface of the body portion with being pressed by the second inflatable bag 26 when the pressures of the bags 28 and 26 raise in the state that the cuff 10 is wound around the ankle 46. And also an outer side surface of the bag 40 changes its form to the same as a form of an inner surface of the bag 26. Consequently, the shape of the envelope of the amplitudes of the pulse waves sensed through the second inflatable bag 40 is definite and an accurate blood pressure is measured thereby because the combination of the bags 26 and 40 fits on the uneven surface of the body portion.

Especially, the invention of this embodiment provides with the most definite shape of the envelope of the amplitudes of the pulse waves sensed through the second inflatable bag 26 because the bag 26 sufficiently fits on the uneven surface of the body portion through the fluid-filled bag 40 and the pulse wave does not propagate from the bag 40 to the first inflatable bag 28 due to the size and the location determined such that the bag 26 and 40 are c overlapped in the state that the cuff 10 is wound around the ankle 46.

While the present invention has been described in its exemplary embodiment, the present invention may be otherwise embodied.

Although, for example, the longitudinal length of the bag 40 is determined such that the bags 26 and 40 are overlapped in the state that the cuff 10 is wound around the ankle 46 in the embodiment described above, the longitudinal length of the fluid-filled bag 40 may be longer or shorter than that of the bag 40 in the embodiment described above. And the transversal length of the bag 40 also may be longer or shorter than the bag 26. More accurate blood pressure is provided by measuring through a bag 26 because the combination of the bag 40 and a part of an inner surface of the bag 26 fits on an uneven surface of a body portion, even though the bag 40 is too small and then a part of the bag 26 is not fit on an uneven surface of the body portion through the bag 40.

It is to be understood that the present invention may be embodied with other changes, improvements, and modifications that may occur to a person skilled in the art without departing from the scope and spirit of the invention defined in the appended claims.

What is claimed is:

1. An inflatable cuff for blood pressure measurement, comprising:
    a first inflatable bag adapted to be wound around a body portion of a living subject and inflatable to press an arterial vessel of the body portion and to stop flow of blood in the arterial vessel;
    a second inflatable bag for sensing a pulse wave propagating along the arterial vessel, the second inflatable bag is supported by the inflatable cuff such that the second inflatable bag is located inside a downstream-side portion of the first inflatable bag as seen in the direction in which the blood flows in the arterial vessel, and which has a dimension as measured in said direction that is smaller than a dimension of the first inflatable bag as measured in said direction;
    a fluid-filled bag that is adapted to be located between the second inflatable bag and the body portion and is filled with incompressible fluid; and
    a shield plate that is located between the first inflatable bag and the second inflatable bag.

2. An apparatus according to claim 1, wherein the incompressible fluid is a liquid.

3. An apparatus according to claim 1, wherein the incompressible fluid is a gel.

4. An apparatus according to claim 1, wherein the fluid-filled bag has a size and is located such that the fluid-filled bag is present in a whole space between the second inflatable bag and the body portion of the living subject in a state that the inflatable cuff is wound around the body portion.

5. An apparatus according to claim 4, wherein the incompressible fluid is a liquid.

6. An apparatus according to claim 4, wherein the incompressible fluid is a gel.

7. An apparatus according to claim 1, wherein the fluid-filled bag has a size and is located such that the second inflatable bag and the fluid-filled bag are overlapped in a state that the inflatable cuff is would around the body portion.

8. An apparatus according to claim 7, wherein the incompressible fluid is a liquid.

9. An apparatus according to claim 7, wherein the incompressible fluid is a gel.

10. An inflatable cuff for blood pressure measurement, comprising:
    a first inflatable bag to be wound around a body portion of a living subject and inflatable to press an arterial vessel of the body portion and to stop flow of blood in the arterial vessel;
    a second inflatable bag for sensing a pulse wave propagating along the arterial vessel, the second inflatable bag is supported by the inflatable cuff such that the second inflatable bag is located inside a downstream-side portion of the first inflatable bag as seen in the direction in which the blood flows in the arterial vessel, and which has a dimension as measured in said direction that is smaller than a dimension of the first inflatable bag as measured in said direction;
    a fluid-filled bag that is adapted to be located between the second inflatable bag and the body portion and is filled with incompressible fluid; and
    a shield plate that is located between the first inflatable bag and the second inflatable bag, the shield plate overlapping only a portion of the first inflatable bag.

11. An apparatus according to claim 10, wherein the second inflatable bag, the fluid-filled bag and the shield plate are fixed together.

12. An apparatus according to claim 10, wherein the second inflatable bag, the fluid-filled bag and the shield plate are sewn together.

13. An apparatus according to claim 11, further comprising a dividing member between the first inflatable bag and the shield plate.

14. An apparatus according to claim 13, wherein the diving member divides an internal space of the inflatable cuff into a first internal space and a second internal space.

15. An apparatus according to claim 14, wherein the first inflatable bag is housed in the first internal space and the second inflatable bag, the shield plate and the fluid-filled bag are housed in the second internal space.

* * * * *